United States Patent [19]

Alminger et al.

[11] Patent Number: 5,021,433

[45] Date of Patent: Jun. 4, 1991

[54] PHARMACOLOGICAL COMPOUNDS COMPOUNDS

[75] Inventors: Tomas B. Alminger, Lindome; Håkan S. Larsson, Göteborg; Per L. Lindberg, Askim; Gunnel E. Sundén, G/ teborg, all of Sweden

[73] Assignee: Aktiebolaget Hassle, Sweden

[21] Appl. No.: 195,343

[22] Filed: May 12, 1988

Related U.S. Application Data

[63] Continuation of Ser. No. 31,008, Nov. 24, 1986.

[30] Foreign Application Priority Data

Oct. 29, 1985 [SE] Sweden .................. 8505112
Oct. 28, 1986 [WO] PCT Int'l Appl. ... PCT/SE86/00493

[51] Int. Cl.$^5$ .................. A61K 31/44; C07D 401/12
[52] U.S. Cl. .................. 514/338; 546/271
[58] Field of Search .................. 546/271; 514/338

[56] References Cited

U.S. PATENT DOCUMENTS 4,435,406  3/1984  Krasso et al. .................. 546/271
4,599,347  7/1986  Krasso et al. .................. 546/271

FOREIGN PATENT DOCUMENTS 176308  4/1986  European Pat. Off. .
644116           Sweden .

OTHER PUBLICATIONS

Fellenius et al., "Substituted Benzimidazoles Inhibit Gastric Acid Secretion by Blocking (H++K+) ATPase", Nature, vol. 290, pp. 159-61, 3/12/81.

Primary Examiner—Jane T. Fan

[57] ABSTRACT

Novel compounds of the formula

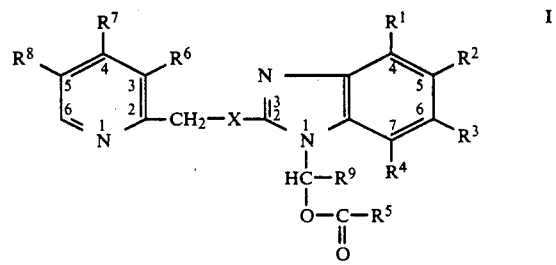

pharmaceutical compositions containing such compounds as active ingredient with gastric and inhibiting effects.

7 Claims, No Drawings

PHARMACOLOGICAL COMPOUNDS

This application is a continuation of application Ser. No. 031,008, filed on Nov. 24, 1986.

FIELD OF THE INVENTION

The object of the present invention is to provide novel compounds, and therapeutically acceptable salts thereof, which inhibit exogenously or endogenously stimulated gastric acid secretion and thus can be used in the prevention and treatment of peptic ulcer.

The present invention relates to the use of the compounds of the invention or therapeutically acceptable salts thereof, for inhibiting gastric acid secretion in mammals and man. In a more general sense, the compounds of the invention may be used for prevention and treatment of gastrointestinal inflammatory diseases in mammals and man, including e.g. gastritis, gastric ulcer, and duodenal ulcer. Furthermore, the compounds may be used for prevention and treatment of other gastrointestinal disorders where gastric antisecretory effect is desirable e.g. in patients with gastrinomas, in patients with acute upper gastrointestinal bleeding, and in patients with a history of chronic and excessive ethanol consumption. The invention also relates to pharmaceutical compositions containing at least one compound of the invention, or a therapeutically acceptable salt thereof, as active ingredient. In a further aspect, the invention relates to processes for preparation of such new compounds, to novel intermediates in the preparation of the compounds of the invention, and to the use of the active compounds for the preparation of pharmaceutical compositions for the medical use indicated above.

PRIOR ART

Benzimidazole derivatives intended for inhibiting gastric acid secretion are disclosed in the British patent specification Nos. 1 500 043 and 1 525 958, in the U.S. Pat. No. 4,182,766, in the European patent specification No. 0 005 129, and in the Belgian patent specification No. 890 024. Benzimidazole derivatives proposed for use in the treatment or prevention of special gastrointestinal inflammatory diseases are disclosed in the European patent application with publication No. 0 045 200.

THE INVENTION

It has been found that the compounds of the formula I are effective as inhibitors of gastric acid secretion in mammals and man:

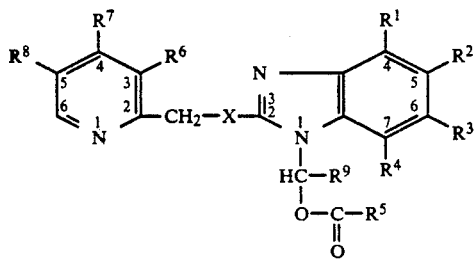

and physiologically acceptable salts thereof, wherein
X is —S— or —SO—;
$R^1$, $R^2$, $R^3$ and $R^4$, which are the same or different, are
(a) H
(b) alkyl containing 1–6 carbon atoms
(c) cycloalkyl containing 3–7 carbon atoms
(d) alkoxy containing 1–6 carbon atoms
(e) alkoxyalkyl containing 1–3 carbon atoms in each alkyl part
(f) alkoxyalkoxy containing 1–3 carbon atoms in each alkyl part
(g) halogen
(h) —CN
(i) —$CF_3$
(j) —$NO_2$
(k) —$COR^{10}$
(l) alkylthio containing 1–6 carbon atoms in the alkyl part
(m) alkylsulfinyl containing 1–7 carbon atoms in the alkyl part
(n) aryl
(o) arylalkyl containing 1–6 carbon atoms in the alkyl part
(p) aryloxy
(q) haloalkoxy containing 1–6 carbon atoms and 1–6 halogen atoms
(r) arylalkoxy containing 1–6 carbon atoms in the alkyl part
(s) $R^1$ and $R^2$, $R^2$ and $R^3$ or $R^3$ and $R^4$ together with the adjacent carbon atoms in the benzimidazole ring form one or more 5-, 6- or 7-membered rings, which each may be saturated or unsaturated and may contain 0–3 hetero atoms selected from N, S and O, and whereby each ring may be optionally substituted with 1–10, suitably 1–6, or 1–4 substituents selected from alkyl groups with 1–3 carbon atoms and halogen, or two or four of the mentioned substituents together form one or two oxo groups

whereby if $R^1$ and $R^2$, $R^2$ and $R^3$ or $R^3$ and $R^4$ together with the adjacent carbon atoms in the benzimidazole ring form two rings the rings may be condensed with each other;

$R^5$ is
(a) alkyl containing 1–6 carbon atoms
(b) mono- or dihydroxy-substituted alkyl containing 1–6 carbon atoms
(c) amino-, monoalkyl (1–3 carbon atoms)-amino-, and dialkyl (1–3 carbon atoms in each alkyl part)-amino-substituted alkyl containing 1–6 carbon atoms, optionally in the form of a salt such as the hydrochloride
(d) carboxy-substituted alkyl containing 1–7 carbon atoms, optionally in the form of a salt such as the sodium or potassium salt
(e) cycloalkyl containing 3–7 carbon atoms
(f) alkoxy containing 1–6 carbon atoms
(g) mono- or dihydroxysubstituted alkoxy containing 1–6 carbon atoms
(h) amino-, monoalkyl (1–3 carbon atoms)-amino-, and dialkyl (1–3 carbon atoms in each alkyl part)-amino-substituted alkoxy containing 1–6 carbon atoms, optionally in the form of a salt such as the hydrochloride
(i) carboxy-substituted alkoxy containing 1–7 carbon atoms, optionally in the form of a salt such as the sodium or potassium salt (j) alkoxyalkoxy containing 1-3 carbon atoms in each alkyl part
(k) alkylamino containing 1-6 carbon atoms
(l) dialkylamino containing 1-4 carbon atoms in each alkyl part
(m) mono- or dicarboxy-substituted alkylamino containing 1-4 carbon atoms in the alkyl part, optionally in the form of a salt, and optionally in esterified form, especially in the form of a mono- or dialkyl ester containing 1-4 carbon atoms in the alkyl part or in the form of a mono- or dibenzyl ester.
(n) aryl, optionally substituted with one or two substituents, which may be the same or different and selected from alkyl containing 1-4 carbon atoms, alkoxy containing 1-4 carbon atoms, halogen, $CF_3$, alkanoyl containing 2-5 carbon atoms, alkoxycarbonyl containing 2-5 carbon atoms, and carboxy, whereby any carboxy group optionally may be in the form of a salt such as the Na salt
(o) aryloxy, optionally substituted with one or two substituents, which may be the same or different and selected from alkyl containing 1-4 carbon atoms, alkoxy containing 1-4 carbon atoms, halogen, $CF_3$, alkanoyl containing 2-5 carbon atoms, alkoxycarbonyl containing 2-5 carbon atoms and carboxy, whereby any carboxy group optionally may be in the form of a salt such as the Na salt
(p) arylalkoxy containing 1-6 carbon atoms in the alkoxy part, wherein the aryl part optionally is substituted with one or two substituents, which may be the same or different and selected from alkyl containing 1-6 carbon atoms, alkoxy containing 1-6 carbon atoms, and carboxy whereby any carboxy group optionally may be in the form of a salt such as the Na salt $R^6$ and $R^8$ are the same or different and selected from
(a) H
(b) alkyl containing 1-6 carbon atoms $R^7$ is
(a) H
(b) alkyl containing 1-7 carbon atoms
(c) alkoxy containing 1-7 carbon atoms
(d) aryl
(e) arylalkyl containing 1-7 carbon atoms in the alkyl part
(f) aryloxy
(g) arylalkoxy containing 1-7 carbon atoms in the alkoxy part
(h) alkenyloxy containing 1-7 carbon atoms in the alkenyl part
(i) alkynyloxy containing 1-7 carbon atoms in the alkynyl part
(j) alkylthio containing 1-7, preferably 1-3 carbon atoms in the alkyl part
(k) arylthio
(l) arylalkylthio containing 1-7, preferably 1-3 carbon atoms in the alkyl part
(m) dialkylamino containing 1-7, preferably 1-3 carbon atoms in each of the alkyl parts
(n) morpholino
(o) piperidino or $R^6$ and $R^7$, or $R^7$ and $R^8$ together with the adjacent carbon atoms in the pyridine ring form a 5- or 6-membered, saturated or unsaturated ring, which may optionally contain an oxygen, sulphur or an optionally alkylated nitrogen atom;

$R^9$ is
(a) H
(b) alkyl containing 1-4 carbon atoms;

$R^{10}$ is
(a) alkyl containing 1-6 carbon atoms
(b) alkoxy containing 1-6 carbon atoms;

with the provisos that
(a) $R^7$ is hydrogen, alkyl, aryl or arylalkyl when the following conditions (a1)-(a3) are fulfilled simultaneously:
(a1) $R^1$ and $R^4$ are both hydrogens
(a2) $R^2$ and $R^3$ are selected from the groups hydrogen, alkyl, alkoxy, $CF_3$ or $COR^{10}$ and
(a3) $R^5$ is alkyl, carboxysubstituted alkyl in its acid form, amino-substituted alkyl, or $R^5$ is aryl optionally substituted by alkyl, alkoxy, halogen or $CF_3$.
(b) $R^5$ is not 2-methylpropoxy when $R^1$, $R^2$, $R^3$, $R^4$, $R^6$, $R^7$, $R^8$, and $R^9$ are hydrogen and X is S.

In addition, the invention includes the two compounds according to examples 2 and 3 below, for the same inventive aspects as the compounds of the formula I.

The compounds of the invention that are sulfoxides (X=SO) have an asymmetric centre in the sulfur atom, i.e. these compounds exist as two optical isomers (enantiomers), or if they also contain one or more asymmetric carbon atoms the compounds have two or more diastereomeric forms, each existing in two enantiomeric forms.

Both the pure enantiomers, racemic mixtures (50% of each enantiomer) and unequal mixtures of the two are within the scope of the present invention. It should be understood that all the diastereomeric forms possible (pure enantiomers or racemic mixtures) are within the scope of the invention.

The compounds of the invention that are sulfides (X=S) may be asymmetric due to one or more asymmetric carbon atoms, as described above. The different diastereomeric forms possible as well as the pure enantiomers and racemic mixtures are within the scope of the invention.

Preferred groups of compounds of the formula I are:
1. Compounds wherein X is —SO—.
2. Compounds wherein X is —S—.
3. Compounds wherein $R^1$, $R^2$, $R^3$ and $R^4$ are the same or different and selected from
   (a) H
   (b) alkyl having 1-6 carbon atoms
   (c) alkoxy having 1-6 carbon atoms in the alkyl part, or
   (d) $R^2$ and $R^3$ together with adjacent carbon atoms in the benzimidazole ring form a saturated or unsaturated 5- or 6-membered ring containing carbon atoms only
   (e) $R^2$ and $R^3$ together with adjacent carbon atoms in the benzimidazole ring form a saturated or unsaturated 5- or 6-membered ring containing carbon and oxygen atoms.
4. Compounds wherein $R^1$, $R^2$, $R^3$ and $R^4$ are H, alkyl containing 1-6 carbon atoms, or alkoxy containing 1-6 carbon atoms.
5. Compounds wherein $R^1$ and $R^4$ are H and $R^2$ and $R^3$ both are alkyl containing 1-6 carbon atoms.
6. Compounds wherein $R^5$ is alkyl containing 1-6 carbon atoms, especially methyl; alkoxy containing 1-6 carbon atoms; aryl, especially phenyl which is unsubstituted or substituted by carboxy, preferably in the form of a salt; mono- and dihydroxysubstituted alkyl containing 1-6 carbon atoms; mono- and dihydroxysubstituted alkoxy containing 1-6 carbon atoms;

carboxy-substituted alkyl containing 1-6 carbon atoms.

6. Compounds wherein $R^5$ is alkyl containing 1-6 carbon atoms; aryl, especially phenyl which is unsubstituted or substituted by carboxy, preferably in the form of a salt; mono- and dihydroxysubstituted alkyl containing 1-6 carbon atoms; mono- dihydroxysubstituted alkoxy containing 1-6 carbon atoms; carboxy-substituted alkyl containing 1-7 carbon atoms, wherein the carboxy group is in the form of a salt; carboxy-substituted alkoxy containing 1-7 carbon atoms wherein the carboxy group may be in the form of a salt; mono- or dicarboxysubstituted alkylamino containing 1-4 carbon atoms in the alkyl part; amino-, monoalkyl (1-3 carbon atoms)-amino-, and dialkyl (1-3 carbon atoms in each alkyl part)-amino-substituted alkyl containing 1-6 carbon atoms, optionally in the form of a salt such as the hydrochloride; and amino-, monoalkyl (1-3 carbon atoms)-amino-, and dialkyl (1-3 carbon atoms in each alkyl part)-amino-substituted alkoxy containing 1-6 carbon atoms, optionally in the form of a salt such as the hydrochloride.

7. Compounds wherein $R^5$ is carboxy-substituted phenyl, preferably with the carboxy group in position 4 of the phenyl ring.

8. Compounds wherein $R^5$ is dialkyl (1-3 carbon atoms)-amino-substituted alkyl (1-6 carbon atoms) in the form of a salt.

9. Compounds wherein $R^5$ is dialkyl (1-3 carbon atoms)-amino-substituted alkoxy containing 1-6 carbon atoms in the form of a salt.

10. Compounds wherein $R^1$, $R^2$, $R^3$ and $R^4$ all are H.

11. Compounds wherein $R^1$ and $R^4$ are alkyl containing 1-6 carbon atoms when $R^2$ and $R^3$ are H.

12. Compounds wherein $R^1$, $R^3$ and $R^4$ are H and $R^2$ is $OCH_3$ or $R^1$, $R^2$ and $R^4$ are H and $R^3$ is $OCH_3$.

13. Compounds wherein $R^7$ is H, alkyl containing 1-6 carbon atoms or alkoxy containing 1-6 carbon atoms.

14. Compounds wherein $R^7$ is alkyl containing 1-6 carbon atoms or alkoxy containing 1-6 carbon atoms.

15. Compounds wherein $R^7$ is alkoxy containing 1-6 carbon atoms.

16. Compounds wherein $R^9$ is H or $CH_3$, especially H.

17. Preferred substituents in position 1 of the benzimidazole nucleus are:
—$CH(CH_3)OCOOC_2H_5$
—$CH_2OCOOC_2H_5$
—$CH_2OCOOCH_2CH(CH_3)_3$
—$CH_2OCOOCH_2CH(OH)CH_2OH$
—$CH_2OCOCH_2CH_2CH_2CH_2COO^-Na^+$

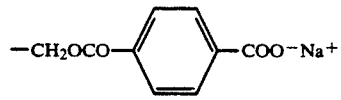

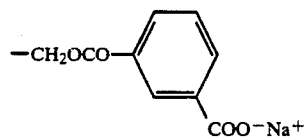

—$CH_2OCOCH_2N(CH_3)$
—$CH_2OCOCH_2N(C_2H_5)_2$
—$CH_2OCOCH_2CH_2N(CH_3)_2$
—$CH_2OCOCH_2CH_2N(C_2H_5)$
—$CH_2OCOCH_2CH_2CH_2N(CH_3)_2$
—$CH_2OCOOCH_2CH_2N(CH_3)_2$
—$CH_2OCOOCH_2N(CH_3)_2$
—$CH_2OCONHCH_2COOH$

whereby the amino-containing groups optionally are in the form of a salt and the carboxy groups optionally are in the form of a salt or an ester.

18. Preferred benzimidazole structures are:

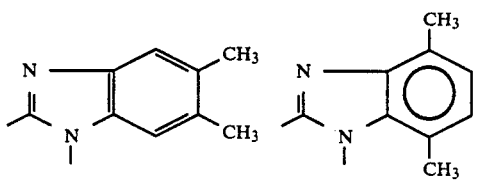

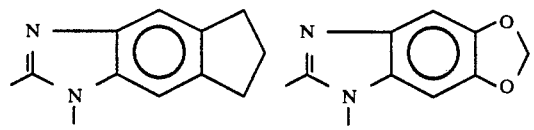

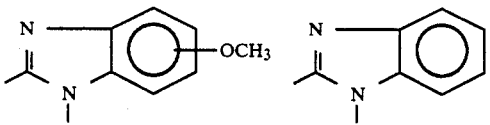

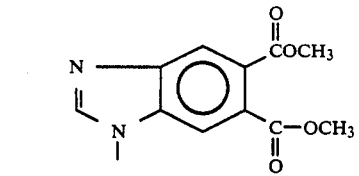

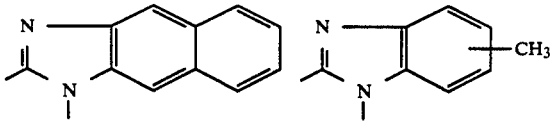

Additional preferred compounds are obtained by combining the indicated preferred meanings for some or all of the radicals X and $R^1$-$R^{10}$ as indicated in the groups 1-18 above. Examples of especially preferred combinations are 19. Combination of 1, 3, 6, 14 and 18.

20. Preferred of the pyridine fragments are:

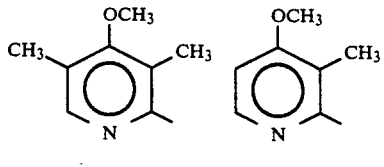

-continued

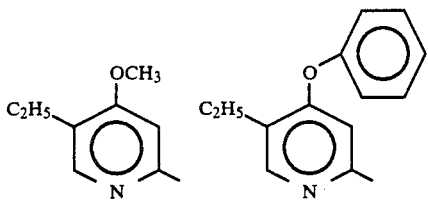

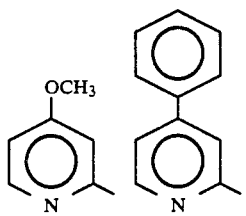

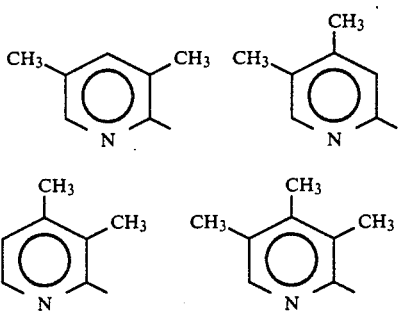

21. Preferred of the pyridine fragments is

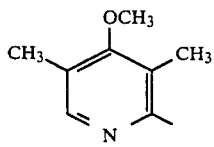

22. Preferred of the pyridinylmethylsulfinyl benzimidazole moieties are

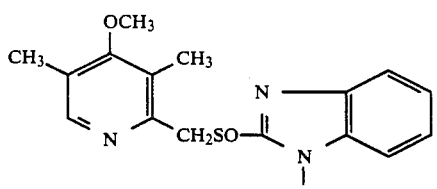

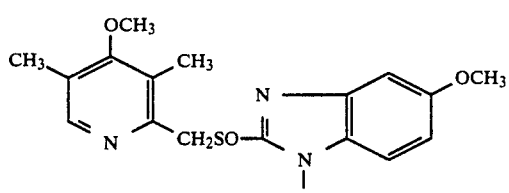

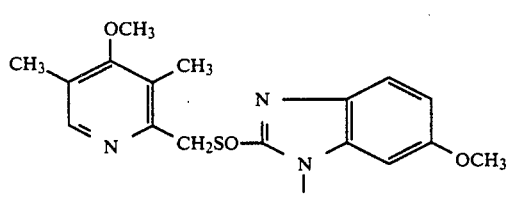

23. Preferred groups of the radicals $R^6$ and $R^8$ are H, $CH_3$ and $C_2H_5$.

The group alkyl in the definitions of $R^1$, $R^2$, $R^3$, $R^4$, $R^5$, $R^6$, $R^7$, $R^8$, and $R^{10}$ is preferably a lower alkyl group having especially preferred 1-4 carbon atoms, e.g. methyl, ethyl, n-propyl, isopropyl, n-butyl or isobutyl.

The group alkoxy in the definitions of $R^1$, $R^2$, $R^3$, $R^4$, $R^7$ and $R^{10}$ is preferably a lower alkoxy group having especially preferred 1-3 carbon atoms, e.g. methoxy, ethoxy, n-propoxy or isopropoxy.

Halogen in the definitions of $R^1$, $R^2$, $R^3$, $R^4$ and $R^5$ is preferably chloro, bromo, fluoro and iodo.

In $R^1$, $R^2$, $R^3$, $R^4$ and $R^7$ when representing alkylthio or alkylsulfinyl is the alkyl preferably a lower alkyl having especially preferred 1-4 carbon atoms, e.g. methylthio, methylsulfinyl, ethylthio, ethylsulfinyl, isopropylthio, n-butylsulfinyl or isobutylthio.

$R^1$, $R^2$, $R^3$, $R^4$, $R^5$ and $R^7$ representing an aryl group have preferably up to 10 carbon atoms, especially preferred up to 6 carbon atoms, e.g. a phenyl group.

$R^1$, $R^2$, $R^3$, $R^4$, $R^5$ and $R^7$ representing an aryloxy group have preferably up to 10 carbon atoms, especially preferred up to 6 carbon atoms, e.g. a phenoxy group.

$R^1$, $R^2$, $R^3$, $R^4$, $R^5$ and $R^7$ representing an arylalkyl or arylalkoxy group have preferably up to 10 carbon atoms in the aryl group. Especially preferred are 6 carbon atoms in the aryl group and 1-3 carbon atoms in the alkyl group or alkoxy group, respectively, e.g. phenylmethyl, phenylethyl, phenylmethoxy, phenylethoxy, phenylpropyl and phenylisopropoxy.

$R^1$, $R^2$, $R^3$, $R^4$ and $R^5$ representing a cycloalkyl group have preferably 3-7 carbon atoms, especially preferred 5-6 carbon atoms, e.g. cyclopentyl, cyclohexyl and methylcyclopentyl.

$R^1$, $R^2$, $R^3$, $R^4$ and $R^5$ representing an alkoxyalkyl or alkoxyalkoxy group have preferably 1-6 carbon atoms in the alkoxy group or groups and alkyl group, respectively, especially preferred 1-3 carbon atoms in the alkoxy group or groups and the alkyl group, respectively, e.g. methoxyethyl, methoxypropyl, ethoxyethyl, propoxyethyl, methoxyethoxy, methoxypropoxy, ethoxyethoxy and propoxyethoxy.

$R^7$ representing an alkenyloxy or alkynyloxy group has preferably 2-7 carbon atoms, especially preferred 3-4 carbon atoms, e.g. allyloxy, propargyloxy, 2-butenyloxy and 2-butynyloxy.

Illustrative examples of ring structures formed by $R^1$ and $R^2$, $R^2$ and $R^3$ and $R^3$ and $R^4$ are $-CH_2CH_2CH_2-$, $-CH_2CH_2CH_2CH_2-$, $-CH_2C(CH_3)_2CH_2-$, $-(CH_2)_5-$, $-CH=CH-CH=CH-$, $-CH_2COCH_2-$, $-OCH_2O-$, $-OCH_2CH_2O-$, $-OCH_2CH_2CH_2O-$, $-OCH_2CH_2-$, $-CH_2CH_2NH-$, $-CH=CH-CH=N-$, $-COCH_2CO-$, $-SCH_2CH_2-$, $-SCH_2S-$, $-SCH_2CH_2S-$, and $-C(CH_3)_2-CO-C(CH_3)_2-$.

$R^6$ and $R^7$, or $R^7$ and $R^8$ representing a 5- or 6-membered saturated or unsaturated ring is preferably a saturated carbocyclic ring or a saturated ring containing an oxygen atom in the 4-position in the pyridine ring, e.g. $-CH_2CH_2CH_2-$, $-CH_2CH_2CH_2CH_2-$, $-O-CH_2CH_2-$, or $-O-CH_2CH_2CH_2-$.

$R^5$ and $R^7$ when representing an alkylamino or dialkylamino group is preferably $-NHCH_3$, $-NHC_2H_5$, $-N(CH_3)_2$, $-N(C_2H_5)_2$, or $-NHCH(CH)_2$.

$R^5$ when representing an amino-, monoalkylamino- and dialkylamino-substituted alkyl group has preferably 1-3 carbon atoms in the alkyl substituent or substituents on the amino group. The amino-, monoalkylamino-or dialkylamino substituent is preferably attached to an alkyl group containing 1–3 carbon atoms.

$R^5$ when representing an amino- monoalkylamino- and dialkylamino-substituted alkoxy group has preferably 1–3 carbon atoms in the alkyl substituent or substituents on the amino group. The amino-, monoalkylamino- or dialkylamino substituent is preferably attached to an alkoxy group containing 1–3 carbon atoms.

For the compounds with the general formula I containing an unsymmetric centre, both the pure enantiomers and the racemic mixtures are within the scope of the present invention.

Further illustrative examples of the radicals in the formula I are given in the examples and lists of specific compounds given elsewhere in this specification.

Illustrative examples of compounds included in the scope of the invention are given in the following Table 1.

The compounds exemplified in examples 8, 13 and 14, are preferred compounds of the invention, whereby the carboxy group may be in the form of a salt. The compounds exemplified in examples 13 and 14 are especially preferred. The carboxy group may be in the form of a salt.

| X  | $R^1$ | $R^2$ | $R^3$ | $R^4$ | $R^5$ | $R^6$ | $R^7$ | $R^8$ | $R^9$ |
|----|-------|-------|-------|-------|-------|-------|-------|-------|-------|
| SO | H | H | H | H | $CH_3$ | $CH_3$ | $OCH_3$ | $CH_3$ | H |
| SO | H | H | H | H | —cyclohexyl | $CH_3$ | $OCH_3$ | $CH_3$ | H |
| SO | H | H | H | H | —cyclopentyl | $CH_3$ | $OCH_3$ | $CH_3$ | H |
| SO | H | H | H | H | —$CH_2$—$CH_2$—phenyl | $CH_3$ | $OCH_3$ | $CH_3$ | H |
| SO |   | H | H | H | —$CH_2$—$CH_2$—$CH_2$—phenyl | $CH_3$ | $OCH_3$ | $CH_3$ | H |
| SO | H | H | H | H | —$CH_2$—$CH_2$—$C_6H_4$—$CH_3$ | $CH_3$ | $OCH_3$ | $CH_3$ | H |
| SO | H | H | H | H | —$OCH_3$ | $CH_3$ | $OCH_3$ | $CH_3$ | H |
| SO | H | H | H | H | —$OCH_2CH_3$ | $CH_3$ | $OCH_3$ | $CH_3$ | H |
| SO | H | H | H | H | —$OCH_2CH_2CH_3$ | $CH_3$ | $OCH_3$ | $CH_3$ | H |
| SO | H | H | H | H | —$O(CH_2)_5CH_3$ | $CH_3$ | $OCH_3$ | $CH_3$ | H |
| SO | H | H | H | H | —$OCH_2OCH_3$ | $CH_3$ | $OCH_3$ | $CH_3$ | H |
| SO | H | H | H | H | —$OCH_2CH_2OCH_3$ | $CH_3$ | $OCH_3$ | $CH_3$ | H |
| SO | H | H | H | H | —$OCH_2CH_2CH_2OCH_3$ | $CH_3$ | $OCH_3$ | $CH_3$ | H |
| SO | H | H | H | H | —$OCH_2OCH_2CH_3$ | $CH_3$ | $OCH_3$ | $CH_3$ | H |
| SO | H | H | H | H | —$OCH_2CH_2OCH_2CH_3$ | $CH_3$ | $OCH_3$ | $CH_3$ | H |
| SO | H | H | H | H | —$OCH_2$—phenyl | $CH_3$ | $OCH_3$ | $CH_3$ | H |
| SO | H | H | H | H | —$OCH_2$—$C_6H_4$—$CH_3$ | $CH_3$ | $OCH_3$ | $CH_3$ | H |
| SO | H | H | H | H | —$OCH_2$—($C_6H_4$)—$CH_3$ (ortho) | $CH_3$ | $OCH_3$ | $CH_3$ | H |

-continued

| X | R¹ | R² | R³ | R⁴ | R⁵ | R⁶ | R⁷ | R⁸ | R⁹ |
|---|----|----|----|----|----|----|----|----|----|
| SO | H | H | H | H | 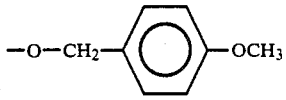 | CH₃ | OCH₃ | CH₃ | H |
| SO | H | H | H | H | 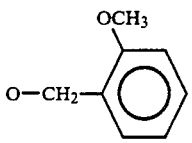 | CH₃ | OCH₃ | CH₃ | H |
| SO | H | H | H | H | 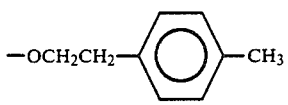 | CH₃ | OCH₃ | CH₃ | H |
| SO | H | H | H | H | 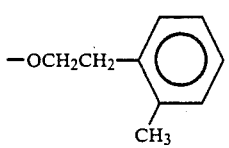 | CH₃ | OCH₃ | CH₃ | H |
| SO | H | H | H | H | 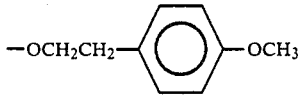 | CH₃ | OCH₃ | CH₃ | H |
| SO | H | H | H | H | 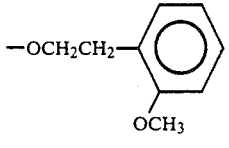 | CH₃ | OCH₃ | CH₃ | H |
| SO | H | H | H | H | —NHCH₃ | CH₃ | OCH₃ | CH₃ | H |
| SO | H | H | H | H | —NHCH₂CH₃ | CH₃ | OCH₃ | CH₃ | H |
| SO | H | H | H | H | —NHCH(CH₃)₂ | CH₃ | OCH₃ | CH₃ | H |
| SO | H | H | H | H | —N(CH₃)₂ | CH₃ | OCH₃ | CH₃ | H |
| SO | CH₃ | H | H | CH₃ | CH₃ | CH₃ | H | CH₃ | CH₃ |
| SO | H | CH₃ | CH₃ | H | CH₂CH₃ | CH₃ | CH₃ | H | CH₃ |
| SO | H |  | | H | C(CH₃)₃ | CH₃ | OCH₃ | CH₃ | H |
| SO | H | —O—CH₂—O— | | H |  | CH₃ | CH₃ | CH₃ | CH₃ |
| SO | H | CH₃ | CH₃ | H | C(CH₃)₃ | CH₃ | H | CH₃ | CH₃ |
| SO | H | CH₃ | CH₃ | H |  | H | H | H | H |
| SO | H | —CH₂—CH₂—CH₂— | | H |  | CH₃ | OCH₃ | CH₃ | CH₃ |
| SO | H | Cl | Cl | H |  | CH₃ | OCH₃ | CH₃ | H |

-continued

| X | R¹ | R² | R³ | R⁴ | R⁵ | R⁶ | R⁷ | R⁸ | R⁹ |
|---|---|---|---|---|---|---|---|---|---|
| SO | H | —CH=CH—CH=CH— | | H | 4-CH₃-C₆H₄— | CH₃ | OCH₃ | CH₃ | CH₃ |
| SO | H | —O—CH₂—O— | | H | 2-CH₃-C₆H₄— | CH₃ | OCH₃ | CH₃ | H |
| SO | H | CH₃ | CH₃ | H | —CH₂CH₂—C₆H₅ | H | OCH₃ | CH₃ | CH₃ |
| SO | H | CH₃ | CH₃ | H | —CH₂CH₂CH₂—C₆H₅ | H | OCH₃ | CH₂CH₃ | CH₃ |
| SO | H | CH₃ | CH₃ | H | —OCH₃ | H | OCH₃ | CH₃ | H |
| SO | H | CH₃ | CH₃ | H | —OC₂H₅ | H | —OCH₂CH₂OCH₃ | H | CH₃ |
| SO | H | CH₃ | CH₃ | H | —OCH₂OCH₃ | H | OCH₃ | COOCH₃ | CH₃ |
| SO | H | COOCH₃ | COOCH₃ | H | —OCH₂—C₆H₅ | CH₃ | H | H | H |
| SO | H | —CH=CH—CH=CH— | | H | —O—CH₂—(4-OCH₃-C₆H₄) | H | H | H | CH₃ |
| SO | H | CH₃ | CH₃ | H | —NHCH₃ | H | C₆H₅ | H | CH₃ |
| SO | H | CH₃ | CH₃ | H | —N(CH₃)₂ | H | CH₃ | H | H |
| SO | H | CH₃ | CH₃ | H | —OCH₂CH₃ | CH₃ | OCH₃ | H | CH₃ |
| SO | H | CH₃ | CH₃ | H | —O—CH(CH₃)₂ | H | OCH(CH₃)₂ | H | H |
| SO | CH₃ | H | H | CH₃ | —OCH₃ | CH₃ | OCH₃ | CH₃ | CH₃ |
| SO | H | H | H | H | OCH₃ | CH₃ | OCH₃ | CH₃ | H |
| SO | H | H | H | H | —O—C₆H₅ | CH₃ | OCH₃ | CH₃ | H |
| SO | H | H | H | H | —NHCH₃ | CH₃ | OCH₃ | CH₃ | H |
| SO | H | H | H | H | OCH₃ | CH₃ | OCH₃ | CH₃ | CH₃ |
| SO | H | H | H | H | —O—C₆H₅ | CH₃ | OCH₃ | CH₃ | CH₃ |
| SO | H | H | H | H | —NHCH₃ | CH₃ | OCH₃ | CH₃ | CH₃ |
| SO | Cl | H | H | Cl | CH₃ | CH₃ | OCH₃ | CH₃ | H |
| SO | H | Cl | Cl | H | CH₂CH₃ | CH₃ | OCH₃ | CH₃ | CH₃ |
| SO | H | Cl | Cl | H | C(CH₃)₃ | CH₃ | OCH₃ | CH₃ | CH₃ |
| SO | Cl | H | H | Cl | —CH₂-cyclobutyl | CH₃ | OCH₃ | CH₃ | H |

-continued

| X | R¹ | R² | R³ | R⁴ | R⁵ | R⁶ | R⁷ | R⁸ | R⁹ |
|---|----|----|----|----|----|----|----|----|----|
| SO | Cl | H | H | Cl |  | $CH_3$ | $OCH_3$ | $CH_3$ | H |
| SO | H | $OCH_3$ | H | H | 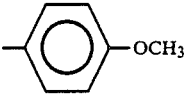 | $CH_3$ | $OCH_3$ | $CH_3$ | $CH_3$ |
| SO | H | $OCH_3$ | H | H | $OCH_3$ | $CH_3$ | $OCH_3$ | $CH_3$ | $CH_3$ |
| SO | H | $OCH_3$ | H | H | $OCH_2CH_3$ | $CH_3$ | $OCH_3$ | $CH_3$ | $CH_3$ |
| SO | H | $OCH_3$ | H | H | 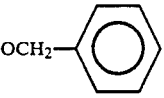 | $CH_3$ | $OCH_3$ | $CH_3$ | H |
| SO | H | $OCH_3$ | H | H | $NHCH_3$ | $CH_3$ | $OCH_3$ | $CH_3$ | $CH_3$ |
| SO | H | H | H | H | $CH_2CH_2CH_2COO^-Na^+$ | $CH_3$ | $OCH_3$ | $CH_3$ | H |
| SO | H | H | H | H | $OCH_2CH(OH)CH_2OH$ | $CH_3$ | $OCH_3$ | $CH_3$ | H |
| SO | H | H | H | H | $OCH_2CH_2\overset{+}{N}H(C_2H_5)_2Cl^-$ | $CH_3$ | $OCH_3$ | $CH_3$ | H |
| SO | H | H | H | H | $CH_2CH_2CH_2\overset{+}{N}H(CH_3)_2Cl^-$ | $CH_3$ | $OCH_3$ | $CH_3$ | H |
| SO | H | $OCH_3$ | H | H | $CH_2CH_2CH_2COO^-Na^+$ | $CH_3$ | $OCH_3$ | $CH_3$ | H |
| SO | H | H | H | H | $CH_2CH_2COO^-Na^+$ | $CH_3$ | $OCH_3$ | $CH_3$ | H |
| SO | H | $OCH_3$ | H | H | $OCH_2CH_2\overset{+}{N}H(CH_3)_2Cl^-$ | $CH_3$ | $OCH_3$ | $CH_3$ | H |

The invention takes into consideration that compounds of formula I may be metabolized before exerting their effect. Such metabolism may occur in the N-substituent in position 1 in the benzimidazole nucleus. Moreover, compounds of the invention wherein X is S are believed to exert their antisecretory activity after metabolism to compounds wherein X is SO. These considerations are also a further aspect of the invention.

Further, it is believed that all compounds of formula I wherein X is SO after administration to a living organism, exert their antisecretory effects after metabolic or pure chemical transformation to another, reactive species. Accordingly, the same is true also for the compounds of formula I wherein X is S, but via initial transformation to the corresponding compounds of formula I wherein X is SO. These considerations as well as such reactive species per se are included within the scope of the present invention.

Preparation

The compounds of the formula I may be prepared by

A. Reacting a compound of the formula II

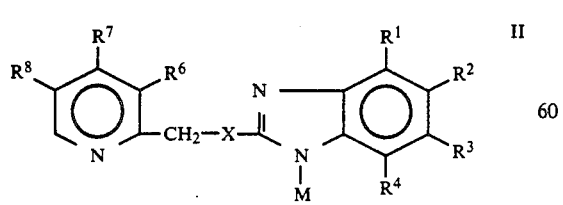

wherein R¹, R², R³, R⁴, R⁶, R⁷, R⁸ and X are as defined under formula I and M is either a metal cation such as Na⁺, K⁺ and Li⁺ or a quaternary ammonium ion, such as tetrabutylammonium with a compound of the formula III

wherein R⁵ and R⁹ are as defined under formula I and Y is halogen such as Cl, Br or I, or a functionally equivalent group.

The reaction of a compound of formula II with a compound of formula III is suitably carried out under protective gas in absence of water. Suitable solvents are hydrocarbons such as toluene and benzene and halogenated hydrocarbons such as methylene chloride and chloroform.

The reaction of the compounds of formula II and III may be carried out at a temperature between the ambient temperature and the boiling temperature of the reaction mixture.

B. Oxidizing a compound of the formula I,

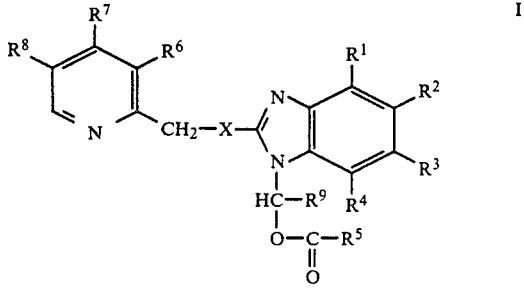

wherein X is S, $R^1$, $R^2$, $R^3$, $R^4$, $R^5$, $R^6$, $R^7$, $R^8$ and $R^9$ have the meanings given, to give a compound of the same formula I wherein X is SO. This oxidation may be carried out by using an oxidizing agent selected from the group consisting of nitric acid, hydrogen peroxide, peracids, peresters, ozone, dinitrogentetraoxide, iodosobenzene, N-halosuccinimide, 1-chlorobenzotriazole, t-butylhypochlorite, diazabicyclo-|2,2,2|-octane bromine complex, sodium metaperiodate, selenium dioxide, manganese dioxide, chromic acid, cericammonium nitrate, bromine, chlorine, and sulfuryl chloride. The oxidation usually takes place in a solvent wherein the oxidizing agent is present in some excess in relation to the product to be oxidized.

The oxidation may also be carried out enzymatically by using an oxidating enzyme or microbiotically by using a suitable microorganism.

C. For the preparation of compounds of the formula I wherein $R^9$ is H, reacting a compound of the formula IV

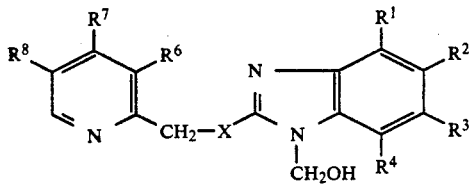

wherein $R^1$, $R^2$, $R^3$, $R^4$, $R^6$, $R^7$, $R^8$ and X are as defined under formula I, with a compound of the formula V

 $R^5COOH$        V or an activated derivative thereof, wherein $R^5$ is as defined under formula I above.

The reaction of a compound of formula IV with a compound of formula V is suitably carried out either directly in the presence of dicyclohexylcarbodiimide and if desired also in the presence of N,N-dimethylaminopyridine (DMAP) or with an activated form of compound V, such as an acid halide or a mixed anhydride or a carbonate.

Suitable solvents are hydrocarbons such as toluene and benzene or halogenated hydrocarbons such as methylene chloride and chloroform or polar solvents such as acetone, dimethyl formamide (DMF), tetrahydrofuran (THF) and pyridine.

The reaction of the compounds of formulas IV and V may be carried out at a temperature between $-15°$ C. and the boiling temperature of the reaction mixture.

D. For preparing compounds of the formula I wherein $R^9$ is H and which contain an amino, monoalkylamino or dialkylamino substituent in the radical $R^5$, reacting a compound of the formula VI

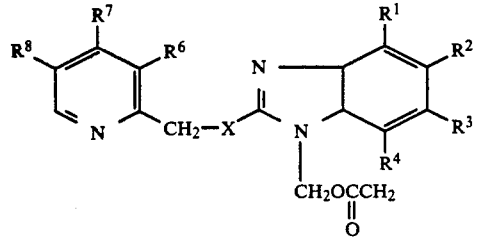

wherein $R^1$, $R^2$, $R^3$, $R^4$, $R^6$, $R^7$, $R^8$ and X are as defined under formula I, and Z is halogen such as Cl, or a functionally equivalent group, with a compound of the formula

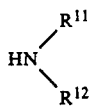

wherein $R^{11}$ and $R^{12}$ are the same or different H or alkyl containing 1–6 carbon atoms.

The reaction is carried out in a suitable solvent such as acetone or acetonitrile at a temperature between the ambient temperature and the boiling temperature of the reaction mixture.

E. For the preparation of compounds of the formula I wherein $R^9$ is H and $R^5$ is monoalkylamino containing 1–6 carbon atoms, reacting a compound of the formula

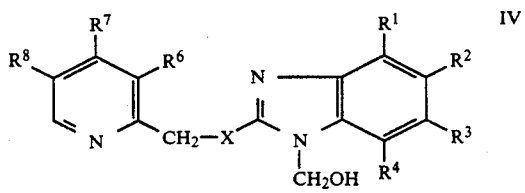

wherein $R^1$, $R^2$, $R^3$, $R^4$, $R^6$, $R^7$, $R^8$ and X are as defined under formula I, with a compound of the formula

 $O=C=N\text{-}R^{13}$      VII wherein $R^{13}$ is alkyl containing 1–6 carbon atoms.

The reaction of a compound of formula VII with a compound of formula IV is carried out either directly or if desired in the presence of a suitable base such as pyridine or N,N-dimethylaminopyridine. Suitable solvents are hydrocarbons such as toluene and benzene or halogenated hydrocarbons such as methylenechloride and chloroform. The reaction of the compounds of formulas IV and VII may be carried out at a temperature between the ambient temperature and the boiling temperature of the reaction mixture.

F. Deblockation of a protecting group in the $R^5$ substituent in a compound of the formula I: This may be done in different ways well known by a person skilled in the art. Thus, for instance, monohydroxyalkyl may be protected as an ester group, which may be deblocked by hydrolysis, geminal dihydroxy-alkyl or geminal dihydroxy-alkoxy groups may be protected as acetonides, which may be deblocked by acid hydrolysis. Amino- and monoalkylamino-alkyl or amino- and monoalkylamino-alkoxy as $R^5$ may be protected by a tert-butyloxycarbonyl (t-Boc) group, which can be deblocked by acid treatment, and a carboxyalkyl or carboxy-alkoxy group as $R^5$ may be protected as an ester, which may be deblocked by hydrolysis.

Depending on the process conditions and the starting materials, the end products of the formula I are obtained either as the free base or as a salt. Both the free base and the salts of these end products are included within the scope of the invention. Thus, salts may be obtained as well as hemi, mono, sesqui or polyhydrates. Acid addition salts of the new compounds may in a manner known per se be transformed into free base using basic agents such as alkali or by ion exchange. The free bases obtained may also form salts with organic or inorganic acids. In the preparation of acid addition salts preferably such acids are used which form suitable therapeutically acceptable salts.

Examples of such acids are hydrohalogen acids, sulfonic acid, phosphoric acid, nitric acid, and perchloric acid; aliphatic, alicyclic, aromatic or heterocyclic carboxyl or sulfonic acids, such as formic acid, acetic acid, propionic acid, succinic acid, glycolic acid, lactic acid, malic acid, tartaric acid, citric acid, ascorbic acid, maleic acid, hydroxymaleic acid, pyruvic acid, phenylacetic acid, benzoic acid, p-aminobenzoic acid, p-hydroxybenzoic acid, salicylic acid or p-aminosalicylic acid, embonic acid, methanesulfonic acid, ethanesulfonic acid, hydroxyethanesulfonic acid, ethylenesulfonic acid, halogenbenzenesulfonic acid, toluenesulfonic acid, naphtylsulfonic acid or sulfanilic acids, methionine, tryptophane, lysine or arginine.

These or other salts of the new sulfide compounds, as e.g. picrates, may serve as purifying agents of the free bases obtained. Salts of the bases may be formed, separated from solution, and then the free base can be recovered in higher purity from a new salt solution.

Racemates obtained can be separated according to known methods, e.g. recrystallization from an optically active solvent, use of microorganisms, reactions with optically active acids forming diastereomeric salts which can be separated, (e.g. separation based on different solubilities of the diastereomers), acylation of a nitrogen or oxygen atom in a substituent by an optically active activated carboxylic acid (e.g. acid chloride), followed by chromatographic separation and deacylation.

Suitable optically active acids for salt formation are the L- and D-forms of tartaric acid, di-o-tolyl-tartaric acid, malic acid, mandelic acid, camphorsulfonic acid or quinic acid, and for acylation O-methylmandelic acid. Preferably the more active part of the two antipodes is isolated.

In the case of diastereomeric mixtures (racemate mixtures) these may be separated into stereoisomeric (diastereomeric) pure racemates by means of chromatography or fractional crystallization.

The starting materials utilized in the methods A-E are in some cases novel. These novel starting materials may, however, be obtained according to processes known per se.

Starting materials of the formulas III, IV, V, VI and VII may be obtained by known methods. Thus, starting materials of the formula III may be obtained from an acid chloride $R^5COCl$ by treatment with a keto-containing compound $R^9CHO$ in the presence of $ZnCl_2$ as is exemplified below. Starting materials of the formula VI may be prepared by reacting a compound of the formula IV with a -halogenated carboxylic acid halide. Starting materials of the formula IV may be prepared as exemplified under "Preparation of intermediates" below.

The compounds of the formulas III, IV, V, VI and VII are in some cases novel and constitute as such part of the invention. This applies in particular to compounds of the formula IV, which thus represent one aspect of the present invention.

The starting materials having $X=S$, utilized in Method B may be obtained according to Method A.

For clinical use the compounds of the invention are formulated into pharmaceutical formulations for oral, rectal, parenteral or other mode of administration. The pharmaceutical formulation contains a compound of the invention in combination with a pharmaceutically acceptable carrier. The carrier may be in the form of a solid, semi-solid or liquid diluent, or a capsule. These pharmaceutical preparations are a further object of the invention. Usually the amount of active compounds is between 0.1–95% by weight of the preparation, between 0.2–20% by weight in preparations for parenteral use and between 1 and 50% by weight in preparations for oral administration.

In the preparation of pharmaceutical formulations containing a compound of the present invention in the form of dosage units for oral administration the compound selected may be mixed with a solid, powdered carrier, such as lactose, saccharose, sorbitol, mannitol, starch, amylopectin, cellulose derivatives, gelatin, or another suitable carrier, as well as with lubricating agents such as magnesium stearate, calcium stearate, sodium stery fumarate and polyethylene glycol waxes. The mixture is then processed into granules or pressed into tablets. Granules and tablets containing sulfoxides may be coated with an enteric coating which protects the active compound from acid degradation as long as the dosage form remains in the stomach. The enteric coating is chosen among pharmaceutically acceptable enteric-coating materials e.g. beeswax, shellac or anionic film-forming polymers such as cellulose acetate phthalate, hydroxypropylmethylcellulose phthalate, partly methyl esterified methacrylic acid polymers and the like, if preferred in combination with a suitable plasticizer. To this coating various dyes may be added in order to distinguish among tablets or granules with different active compounds or with different amounts of the active compound present.

Soft gelatine capsules may be prepared with capsules containing a mixture of the active compound or compounds of the invention, vegetable oil, fat, or other suitable vehicle for soft gelatine capsules. Soft gelatine capsules may also be enteric coated as described above. Hard gelatine capsules may contain granules or enteric-coated granules of the active compound. Hard gelatine capsules may also contain the active compound in combination with a solid powdered carrier such as lactose, saccharose, sorbitol, mannitol, potato starch, amylopectin, cellulose derivatives or gelatine. The hard gelatine capsules may be enteric coated as described above.

Dosage units for rectal administration may be prepared in the form of suppositories which contain the active substance mixed with a neutral fat base, or they may be prepared in the form of a gelatine rectal capsule which contains the active substance in a mixture with a vegetable oil, paraffin oil or other suitable vehicle for gelatine rectal capsules, or they may be prepared in the form of a ready-made micro enema, or they may be prepared in the form of a dry micro enema formulation to be reconstituted in a suitable solvent just prior to administration.

Liquid preparations for oral administration may be prepared in the form of syrups or suspensions, e.g. solutions or suspensions containing from 0.2% to 20% by weight of the active ingredient and the remainder consisting of sugar or sugaralcohols and a mixture of ethanol, water, glycerol, propylene glycol and polyethylene glycol. If desired, such liquid preparations may contain colouring agents, flavouring agents, saccharine and carboxymethyl cellulose or other thickening agents. Liquid preparations for oral administration may also be prepared in the form of a dry powder to be reconstituted with a suitable solvent prior to use.

Solutions for parenteral administration may be prepared as a solution of a compound of the invention in a pharmaceutically acceptable solvent, preferably in a concentration from 0.1% to 10% by weight. These solutions may also contain stabilizing agents and/or buffering agents and may be manufactured in different unit dose ampoules or vials. Solutions for parenteral administration may also be prepared as a dry preparation to be reconstituted with a suitable solvent extemporaneously before use.

The typical daily dose of the active substance varies within a wide range and will depend on various factors such as for example the individual requirement of each patient, the route of administration and the disease. In general, oral and parenteral dosages will be in the range of 5 to 500 mg per day of active substance.

The invention is illustrated by the following examples.

EXAMPLE 1

Preparation of acetic acid, [2-[[(3,5-dimethyl-4-methoxy-2-pyridinyl)methyl]sulfinyl]-1H-benzimidazol-1-yl]methyl ester sodium salt To NaOH (0.48 g 0.012 mol) dissolved in $H_2O$ (20 ml) was added under stirring 2-[[(3,5-dimethyl-4-methoxy-2-pyridinyl)methyl]sulfinyl]-1H-benzimidazole (1.89 g 0.006 mol) and tetrabutylammoniumhydrogen sulfate (2.04 g 0.006 mol). The mixture was stirred for about 5 min at ambient temperature and then extracted 3 times with $CH_2Cl_2$ (30 ml). After separation the combined $CH_2Cl_2$ phases were dried over $Na_2SO_4$, filtrated and the solvent evaporated off giving an oil. The residual oil was dissolved in toluene (40 ml) and heated to +60° C. Chloromethyl acetate (0.72 g 0.0066 mol) dissolved in dry toluene (10 ml) was added under a protective gas and under stirring. The solution was allowed to stand over night at +60° C. The toluene was evaporated off and the residual oil was chromatographed on a silica column using $CH_3OH$—$CH_2Cl_2$ (5:95) as eluent and then the product was recrystallized from isopropylether giving the product (0.39 g 17%). The identity of the title product obtained was confirmed with NMR.

EXAMPLES 2–6

The compounds listed under Examples 2–6 below were prepared using the method exemplified in Example 1.

EXAMPLE 7

Preparation of adipic acid, [2-[[(3,5-dimethyl-4-methoxy-2-pyridinyl)methyl]sulfinyl]-1H-benzimidazol-1-yl]methyl monoester sodium salt Adipic acid, [2-[[3,5-dimethyl-4-methoxy-2-pyridinyl)methyl]sulfinyl]-1H-benzimidazol-1-yl]methyl chloromethyl ester (0.60 g, 0.0011 mol) (synthesized according to method A) was dissolved in 50% aqueous acetonitrile (40 ml) and three equivalents of aqueous NaOH was added slowly under continuous stirring. The acetonitrile was evaporated off, the residue was washed with $CH_2Cl_2$, and the residual water was evaporated giving an oily residue. Chromatography on $SiO_2$ with ethyl acetate-ethanol as eluent gave the desired compound (0.02 g). The identity of the product was confirmed with NMR.

EXAMPLE 8

Preparation of terephtalic acid, [2-[[(4-methoxy-3,5-dimethyl-2-pyridinyl)methyl]sulfinyl]-1H-benzimidazol-1-yl]-methyl monoester sodium salt (Method C)

To terephthalic acid (166 g 0.01 mol) in THF (50 ml) was added diisopropylethyl amin (2.6 g 0.02 mol) and the mixture was cooled to −10° C. Isobutylchloroformate (1.36 g 0.01 mol) dissolved in THF (20 ml) was added dropwise under stirring. After the addition, the temperature of the mixture was raised to +15° and [2-[[(4-methoxy-3,5-dimethyl-2-pyridinyl)methyl]sulfinyl]-1H-benzimidazol-1-yl]methanol dissolved in THF (20 ml) was added dropwise. The mixture was stirred 2 h at room temperature. THF was evaporated and the residue was dissolved in $CH_2Cl_2$ and washed with water. After separation the $CH_2Cl_2$ phase was evaporated. The residual oil was dissolved in ethylacetate, $H_2O$ was added and the pH was adjusted to 2.5 with NaOH (1M). After separation the ethylacetate phase was evaporated and the residue was dissolved in $CH_2Cl_2$, dried over $Na_2SO_4$, filtered and the solvent was evaporated, giving the desired compound (yield 0.8 g, 16%). The identity of the title compound obtained was confirmed with NMR.

EXAMPLE 9

Preparation of N,N-dimethyl-β-alanine, [2-[[(4-methoxy-3,5-dimethyl-2-pyridinyl)methyl]sulfinyl]-1H-benzimidazol-1-yl]-methyl ester (Method C)

N,N-dimethyl-β-alanine (0.76 g 0.005 mol) and N-methyl morpholine (0.99 g 0.01 mol) was added to $CH_2Cl_2$ (15 ml). The solution was cooled to −10° C. and isobutylchloroformate, (0.68 g 0.005 mol) dissolved in $CH_2Cl_2$ (15 ml), was added under inert atmosphere. The solution was stirred for about 20 min at −10° C. [2-[[(4-methoxy-3,5-dimethyl-2-pyridinyl)methyl]sulfinyl]-1H-benzimidazol-1-yl]methanol dissolved in $CH_2Cl_2$ (15 ml) was added dropwise to the mixed anhydride at −10° C. The solution was stirred 2 h at −10°, and the temperature was thereafter raised to room temperature. NaOH solution (25 ml 0.24) was added under stirring and the mixture was stirred for about 5 min. After separation the $CH_2Cl_2$ phase was dried over $Na_2SO_4$, filtered and the solution was evaporated off, giving the desired compound (yield 0.7 g 32%). The identity of the title compound was confirmed with NMR. Melting point: >230°.

EXAMPLES 10 AND 12

The compounds listed under Examples 10 and 12 in Table 2 were prepared by Method C.

EXAMPLES 13 AND 14

The compounds listed under Examples 13 and 14 in Table 2 can be prepared by Method C.

EXAMPLE 11

N,N-diethylglycine, [2[[(4-methoxy-3,5-dimethyl-2-pyridinyl)methyl]sulfinyl]-1H-benzimidazol-1-yl]methyl ester (Method C)

A mixture of [2[[(4-methoxy-3,5-dimethyl-2-pyridinyl)methyl]sulfinyl]-1H-benzimidazol-1-yl]methanol (3.5 g 0.010 mol), N,N-dicyclohexylcarbodiimide (2.1 g 0.010 mol), N,N-diethylglycine hydrochloride (1.7 g 0.010 mol) and 4-dimethylaminopyridine (1.3 g 0.011 mol) in pyridine (75 ml) was stirred at room temperature for 39 h. N,N-dicyclohexyl urea which had precipitated was removed by filtration. The filtrate was evaporated, the residue was dissolved in dichloromethane. The dichloromethanesolution was washed with NaOH 0.080 g (0.0020 mol), dissolved in water (25 ml) and then once with water (25 ml). The organic phase was dried ($Na_2SO_4$), filtered and the solvent was evaporated off, giving the desired product. The identity of the product was confirmed with NMR.

TABLE 2
Summary of Examples 1-14

| Ex. | X | $R^1$ | $R^2$ | $R^3$ | $R^4$ | $R^5$ | $R^6$ | $R^7$ | $R^8$ | $R^9$ | Yield % | Identifying data |
|---|---|---|---|---|---|---|---|---|---|---|---|---|
| 1 | SO | H | $CH_3$ | $CH_3$ | H | $C(CH_3)_3$ | $CH_3$ | H | $CH_3$ | H | 57 | NMR |
| 2 | SO | H | H | H | H | $-CH_3$ | $CH_3$ | $OCH_3$ | $CH_3$ | H | 17 | NMR |
| 3 | SO | H | H | H | H | —C$_6$H$_{11}$ (cyclohexyl) | $CH_3$ | $OCH_3$ | $CH_3$ | H | 22 | NMR |
| 4 | SO | H | H | H | H | $-OC_2H_5$ | $CH_3$ | $OCH_3$ | $CH_3$ | $CH_3$ | 12 | NMR |
| 5 | SO | H | H | H | H | $-OC_2H_5$ | $CH_3$ | $OCH_3$ | $CH_3$ | H | 56 | NMR |
| 6 | SO | H | H | H | H | $OCH_2CHOHCH_2OH$ | $CH_3$ | $OCH_3$ | $CH_3$ | H | | NMR |
| 7 | SO | H | H | H | H | $(CH_2)_4COO^-Na^+$ | $CH_3$ | $OCH_3$ | $CH_3$ | H | | NMR |
| 8 | SO | H | H | H | H | —C$_6$H$_4$—COO$^-$Na$^+$ | $CH_3$ | $OCH_3$ | $CH_3$ | H | 16 | NMR |
| 9 | SO | H | H | H | H | $-(CH_2)_2-N(CH_3)_2$ | $CH_3$ | $OCH_3$ | $CH_3$ | H | 32 | NMR |
| 10 | SO | H | H | H | H | $-NHCH_2COOCH_2-$C$_6$H$_5$ | $CH_3$ | $OCH_3$ | $CH_3$ | H | | NMR |
| 11 | SO | H | H | H | H | $-CH_2-N(C_2H_5)_2$ | $CH_3$ | $OCH_3$ | $CH_3$ | H | | NMR |
| 12 | SO | H | H | H | H | $OCH_2CH(CH_3)_2$ | $CH_3$ | $OCH_3$ | $CH_3$ | H | | NMR |
| 13 | SO | H | $OCH_3$ | H | H | —C$_6$H$_4$—COO$^-$NH$^+$(C$_2$H$_5$)(CH(CH$_3$)$_2$) | $CH_3$ | $OCH_3$ | $CH_3$ | H | | NMR |
| 14 | SO | H | H | $OCH_3$ | H | —C$_6$H$_4$—COO$^-$NH$^+$(C$_2$H$_5$)(CH(CH$_3$)$_2$) | $CH_3$ | $OCH_3$ | $CH_3$ | H | | NMR |

Identifying data for the compounds according to examples 1-14 are given in Table 3 below.

TABLE 3
Identifying data for compounds of the invention

| Ex. | Solvent | NMR data δ ppm (500 MHz) |
|---|---|---|
| 1 | $CDCl_3$ | 1.15 (s, 9H), 2.3 (s, 3H), 2.35 (s, 3H), 2.4 (s, 3H), 2.45 (s, 3H), 4.9-5.0 (q, 2H), 6.35-6.40 (q, 2H), 7.3 (s, 1H), 7.35 (s, 1H), 7.55 (s, 1H), 8.2 (s, 1H) |
| 2 | $CDCl_3$ | 2.5 (s, 3H), 2.6 (s, 3H), 2.7 (s, 3H), 4.15 (s, 3H), 5.35 (s, 2H), 6.85-6.95 (q, 2H), 7.75-7.9 (m, 2H), 8.5 (d, 1H), 8.25 (d, 1H), 8.55 (s, 1H) |
| 3 | $CDCl_3$ | 2.2 (s, 3H), 2.25 (s, 3H), 3.7 (s, 3H), 4.95-5.1 (q, 2H), 6.7-6.8 (q, 2H), 7.3-7.5 (m, 4H), 7.55 (t, 1H), 7.75 (d, 1H), 7.85 (d, 1H), 8.05 (d, 2H), 8.15 (s, 1H) |
| 4 | $CD_3OD$ | 1.3 (t, 3H), 2.0 (d, 3H), 2.3 (s, 6H), 3.8 (s, 3H), 4.2-4.35 (m, 4H), 5.0 (d, 1H), 5.2 (d, 1H), 7.4-7.6 (m, 2H), 7.8 (d, 1H), 7.9 (d, 1H), 9.2 (s, 1H) |
| 5 | $CDCl_3$ | 1.25 (t, 3H), 2.15 (s, 3H), 2.25 (s, 3H), 3.7 (s, 3H), 4.05-4.4 (q, 2H), 5.0 (s, 2H), 6.35-6.75 (q, 2H), 7.35-8.0 (m, 4H), 8.2 (s, 1H) |
| 6 | (90 MHz) $CDCl_3$ | 2.15 (s, 3H), 2.20 (s, 3H), 3.55-5.05 (m, 12H), 6.55 (dd, 2H), 7.3-7.95 (m, 4H), 8.2 (s, 1H) |
| 7 | (500 MHz) $CD_3OD$ | 1.55-1.75 (m, 4H), 2.25 (s, 3H), 2.3 (s, 3H), 2.25 (t, 3H), 2.45 (t, 2H), 3.8 (s, 3H), 5.05 (dd, 2H), 6.5 (dd, 2H), 7.45 (dd, 1H), 7.5 (dd, 1H), 7.55-7.65 (m, 2H), 8.10 (s, 1H) |
| 8 | DMSO | 2.1 (s, 3H), 2.15 (s, 3H), 3.65 (s, 3H), 4.8-5.05 (q, 2H) |

TABLE 3-continued

Identifying data for compounds of the invention

| Ex. | Solvent | NMR data δ ppm (500 MHz) |
|---|---|---|
|  |  | 6.7 (d, 2H), 7.35 (t, 1H), 7.45 (t, 1H), 7.75 (d, 1H), 7.8-8 (m, 4H), 8.05 (s, 1H) |
| 9 | CDCl$_3$ | 2.15 (s, 6H), 2.2 (s, 3H), 2.25 (s, 3H), 2.26 (t, 2H), 3.75 (s, 3H), 4.95 (s, 2H), 6.4–6.55 (q, 2H), 7.25-7.5 (m, 2H), 7.6 (d, 1H), 7.8 (d, 1H), 8.1 (s, 1H) |
| 10 | CDCl$_3$ | 2.25 (s, 3H), 2.4 (s, 3H), 3.8 (s, 3H), 4.85 (s, 2H), 5.4 (s, 2H), 6.4 (s, 2H), 7.3 (d, 1H), 7.35-7.5 (m, 2H), 7.65 (d, 1H), 8.05-8.15 (q, 4H), 8.25 (s, 1H) |
| 11 | (90 MHz) CDCl$_3$ | 0.85-1.0 (t, 6H), 2.15 (s, 3H), 2.25 (s, 3H), 2.45-2.7 (q, 4H), 3.4 (s, 2H), 3.7 (s, 3H), 5.0 (s, 2H), 6.55 (s, 2H), 7.3-7.95 (m, 4H), 8.2 (s, 1H) |
| 12 | CDCl$_3$ | 0.9 (d, 6H), 1.95 (m, 1H), 2.2 (s, 3H), 2.3 (s, 3H), 3.95 (d, 2H), 4.95-5.05 (q, 2H), 6.45-6.65 (q, 2H), 7.4-7.55 (m, 2H), 7.7 (d, 1H), 7.85 (d, 1H), 8.2 (s, 1H) |
| 13+14 (the anionic part) | CDCl$_3$ | 2.2 (s,3H), 2.25 (s,3H), 3.7 (s,3H), 3.85 and 3.9 (2s, tot. 3H), 5.0–5.1 (q, 2H), 6.65–6.75 (2q, tot. 2H), 7.0 and 7.1 (2d, tot. 1H), 7.2 and 7.3 (2s, tot. 1H), 7.6 and 7.65 (2d, tot. 1H), 8.05 (m, 4H), 8.2 (s, 1H) |

PREPARATION OF INTERMEDIATES

Preparation of chloromethylbenzoate

Benzyl chloride (35 g, 0.25 mol) and fused ZnCl$_2$ (1.0 g, 0.0073 mol) were heated in the presence of dry paraformaldehyde (7.5 g, 0.75 mol) for 2 h giving an oil, which was distilled in vacuo giving the desired compound (175 g, 41%). The identity of the product was confirmed with NMR; δ(500 MHz; CDCl$_3$) 6.0 (s, 2H), 7.5 (dd, 2H), 7.65 (t, 1H), 8.1 (d, 2H).

Preparation of [2-[[(4-Methoxy-3,5-dimethyl-2-pyridinyl)methyl)sulfinyl]-1H-benzimidazol-1-yl]methanol 2-[[(4-Methoxy-3,5-dimethyl-2-pyridinyl)methyl]sulfinyl]-1H-benzimidazole (3.15 g, 10 mmoles) and N,N-dimethylaminopyridine (120 mg, 1 mmol) was dissolved in methylene chloride (50 ml). A solution of formaldehyde (5M, 10 ml, 50 mmol) was added and the mixture was stirred violently for 2 minutes. The phases were separated and the methylene chloride solution was dried (sodium sulphate), filtered and evaporated to dryness. The slightly red residue was the title compound as an essentially pure oil.

NMR: 500 MHz, CDCl$_3$, δ: 2.15, 2.27, 3.70, 4.89, 5.89, 7.33, 7.63, 7.96.

Pharmaceutical preparations containing a compound of the invention as active ingredient are illustrated in the following formulations.

Syrup

A syrup containing 1% (weight per volume) of active substance was prepared from the following ingredients:
Compound according to Example 7: 1.0 g.
Sugar, powder: 30.0 g.
Saccharine: 0.6 g.
Glycerol: 5.0 g.
Flavouring agent: 0.05 g.
Ethanol 96%: 5.0 g.
Distilled water q.s. to a final volume of 100 ml.

Sugar and saccharine were dissolved in 60 g of warm water. After cooling the active compound was added to the sugar solution and glycerol and a solution of flavouring agents dissolved in ethanol were added. The mixture was diluted with water to a final volume of 100 ml.

Enteric-coated tablets

An enteric-coated tablet containing 20 mg of active compound was prepared from the following ingredients:

I Compound according to Example 5: 200 g.
Lactose: 700 g.
Methyl cellulose: 6 g.
Polyvinylpyrrolidone cross-linked: 50 g.
Magnesium stearate: 15 g.
Sodium carbonate: 6 g.
Distilled water: q.s.
II Cellulose acetate phthalate: 200 g.
Cetyl alcohol: 15 g.
Isopropanol: 2000 g.
Methylene chloride: 2000 g.

I Compound according to example 5, powder, was mixed with lactose and granulated with a water solution of methyl cellulose and sodium carbonate. The wet mass was forced through a sieve and the granulate dried in an oven. After drying the granulate was mixed with polyvinylpyrrolidone and magnesium stearate. The dry mixture was pressed into tablet cores (10 000 tabelst), each tablet containing 20 mg of active substance, in a tabletting machine using 6 mm diameter punches.

II A solution of cellulose acetate phthalate and cetyl alcohol in isopropanol/methylene chloride was sprayed onto the tablets I in an Accela Cota ®, Manesty coating equipment. A final tablet weight of 110 mg was obtained.

Solution for intravenous administration

A parenteral formulation for intravenous use, containing 4 mg of active compound per ml, was prepared from the following ingredients:
Compound according to Example 8: 4 g.
Polyethylene glycol 400 for injection: 400 g.
Disodium hydrogen phosphate: q.s.
Sterile water to a final volume of 1000 ml.

The active compound was dissolved in polyethylene glycol 400 and 550 ml of water was added. pH of the solution was brought to pH 7.4 by adding a water solution of disodium hydrogen phosphate and water was added to a final volume of 1000 ml. The solution was filtered through a 0.22 μm filter and immediately dispensed into 10 ml sterile ampoules. The ampoules were sealed.

BIOLOGICAL TESTS

Inhibiting effect in vivo on gastric acid secretion in conscious dog

Test method

Chronic gastric fistula dog were used. These dogs have been surgically provided with a gastric cannula in the stomach and a duodenal fistula, used for direct intraduodenal administration of test compounds. Following a 4 weeks' recovery period after surgery, tests were performed once a week on each dog. Food and water were withdrawn 18 hours before each test.

The test compound suspended in 0.5% Methocel ® (90 HG 15000, Dow Chem Corp) was administered either orally by using a stomach tube or intraduodenally via a catheter through the duodenal fistula. After 1 hour gastric acid secretion was induced by continuous infusion of histamine at individual doses (400–600 μmol/kg, h), resulting in approx 90% of maximal secretion of gastric acid. The gastric juice was collected by free flow from the gastric cannula in consecutive 30 min samples for 2 hours. The samples were titrated to pH 7.0 with 0.1M NaOH using a Radiometer automatic titrator and the acid output was calculated. The percent inhibition of acid secretion was calculated by comparing in each dog the acid output in control tests when only the vehicle was given. The peak inhibitory effect for each compound was determined.

The test results are given in Table 4 below.

TABLE 4

Gastric acid inhibition in the dog

| Test compound | Administered amount of test compound (oral administration, μmol) | Inhibition of gastric acid secretion |
|---|---|---|
| Example 2 | 8 | 75% |
| Example 3 | 2 | 95% |

What we claim is:

1. A compound of the formula

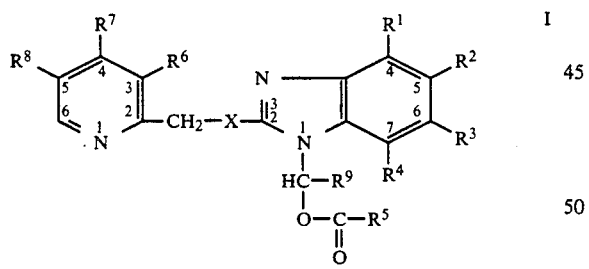

or physiologically acceptable salts thereof, wherein
X is —S— or —SO—;
$R^1$, $R^2$, $R^3$ and $R^4$, which are the same or different, are
(a) H
(b) alkyl containing 1–6 carbon atoms
(c) cycloalkyl containing 3–7 carbon atoms
(d) alkoxy containing 1–6 carbon atoms
(e) alkoxyalkyl containing 1–3 carbon atoms in each alkyl part
(f) alkoxyalkoxy containing 1–3 carbon atoms in each alkyl part
(g) halogen
(h) —CN
(i) —CF$_3$
(j) —NO$_2$
(k) —COR$^{10}$
(l) alkylthio containing 1–6 carbon atoms in the alkyl part
(m) alkylsulfinyl containing 1–7 carbon atoms in the alkyl part
(n) phenyl
(o) phenylalkyl containing 1–6 carbon atoms in the alkyl part
(p) phenoxy
(q) haloalkoxy containing 1–6 carbon atoms and 1–6 halogen atoms
(r) phenylalkoxy containing 1–6 carbon atoms in the alkyl part $R^5$ is selected from the group consisting of a dialkyl (1–3 carbon atoms)-amino-substituted alkoxy containing 1–6 carbon atoms in the form of a salt and a carboxy-substituted phenyl, $R^6$ and $R^8$ are the same or different and selected from
(a) H
(b) alkyl containing 1–6 carbon atoms $R^7$ is
(a) H
(b) alkyl containing 1–7 carbon atoms
(c) alkoxy containing 1–7 carbon atoms
(d) phenyl
(e) phenylalkyl containing 1–7 carbon atoms in the alkyl part
(f) phenoxy
(g) phenylalkoxy containing 1–7 carbon atoms in the alkoxy part
(h) alkenyloxy containing 1–7 carbon atoms in the alkenyl part
(i) alkynyloxy containing 1–7 carbon atoms in the alkynyl part
(j) alkylthio containing 1–7, preferably 1–3 carbon atoms in the alkyl part
(k) phenylthio
(l) phenylakylthio containing 1–7, preferably 1–3 carbon atoms in the alkyl part
(m) dialkylamino containing 1–7, preferably 1–3 carbon atoms in each of the alkyl parts
(n) morpholino
(o) piperidino $R^9$ is
(a) H
(b) alkyl containing 1–4 carbon atoms;

$R^{10}$ is
(a) alkyl containing 1–6 carbon atoms
(b) alkoxy containing 1–6 carbon atoms.

2. A compound of the formula

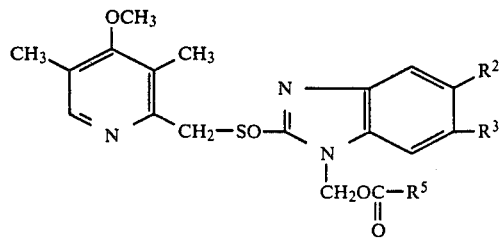

or a physiologically acceptable salt thereof, wherein $R^2$, $R^3$ and $R^5$ are combined as follows:

| R² | R³ | R⁵ |
|---|---|---|
| H | H | 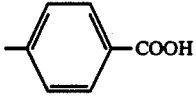 |
| OCH₃ | H | 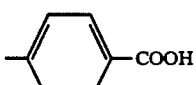 |
| H | OCH₃ | 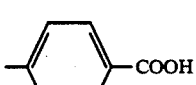 |
| OCH₃ | H | 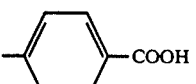 |
| H | OCH₃ | 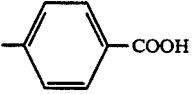 |

3. A compound according to claim 2, or a physiologically acceptable salt thereof, wherein R², R³ and R⁵ are combined as follows:

4. A compound according to claim 1 wherein in R⁵ the carboxy group is in position 4 on the phenyl ring.

5. A pharmaceutical composition for use in the control of gastric acid secretion and the treatment of gastrointestinal inflammatory diseases in mammals including man comprising an effective amount of a compound according to claims 1, 2 or 3, together with a pharmaceutically acceptable carrier.

6. A method for inhibiting gastric acid secretion in mammals including man comprising administering to a mammal an effective amount of a compound as defined in claims 1, 2 or 3.

7. A method for treating gastrointestinal inflammatory diseases in mammals including man, comprising administering to a mammal an effective amount of a compound as defined in claims 1, 2 or 3.

* * * * *

UNITED STATES PATENT AND TRADEMARK OFFICE
CERTIFICATE OF CORRECTION

PATENT NO. : 5,021,433

DATED : June 4, 1991

INVENTOR(S) : Tomas B. Alminger; Hakan S. Larsson; Per L. Lindberg; Gunnel E. Sunden It is certified that error appears in the above-identified patent and that said Letters Patent is hereby corrected as shown below:

Cover page, item [54], after "COMPOUNDS"
   delete --COMPOUNDS--;

Cover page, item [75] Inventors, "G\ teborg"
   should read --Göteborg--;

Cover page, item [57] Abstract, "and" should read --acid--;

col. 5, delete lines 1 through 7;

col. 5, line 8, before "car-"
   delete --stituted alkoxy containing 1-6 carbon atoms;--;

col. 21 line 24, after "salt" insert --(Method A)--;

UNITED STATES PATENT AND TRADEMARK OFFICE
CERTIFICATE OF CORRECTION

PATENT NO. : 5,021,433

DATED : June 4, 1991

INVENTOR(S) : Tomas B. Alminger et al.

It is certified that error appears in the above-identified patent and that said Letters Patent is hereby corrected as shown below:

col. 26, line 44, "tabelst" should read --tablets--;

Signed and Sealed this

Twenty-fourth Day of November, 1992

Attest:

DOUGLAS B. COMER

Attesting Officer

Acting Commissioner of Patents and Trademarks